United States Patent [19]

Nelson

[11] 4,074,433
[45] Feb. 21, 1978

[54] INTERMAXILLARY TOOTH MOVING DEVICE

[75] Inventor: John E. Nelson, Holtwood, Pa.

[73] Assignee: Hamilton Technology, Inc., Lancaster, Pa.

[21] Appl. No.: 720,837

[22] Filed: Sept. 7, 1976

[51] Int. Cl.² .............................................. A61C 7/00
[52] U.S. Cl. ................................................... 32/14 E
[58] Field of Search ............................. 32/14 B, 14 E

[56] References Cited

U.S. PATENT DOCUMENTS

| 3,654,702 | 4/1972 | Kelly | 32/14 E |
| 3,921,295 | 11/1975 | James | 32/14 A |

*Primary Examiner*—Robert Peshock
*Attorney, Agent, or Firm*—LeBlanc & Shur

[57] ABSTRACT

Disclosed is an orthodontic appliance for intermaxillary tooth correction comprising a pair of housings adapted to be connected to teeth in the upper and lower jaws respectively. Each housing has a pulley joined together by a pull cable with springs acting to draw the ends of the cable in opposite directions. The cables are wound in opposite directions so that the cable ends need not be centered in the housings. This facilitates assembly of the devices in which both are made of identical parts for ease of manufacture.

18 Claims, 16 Drawing Figures

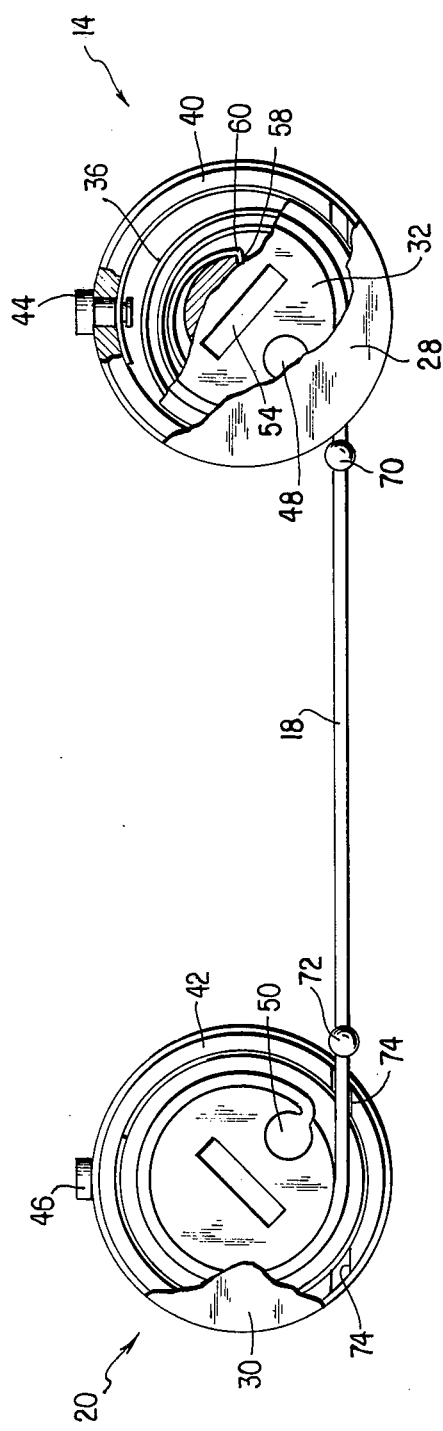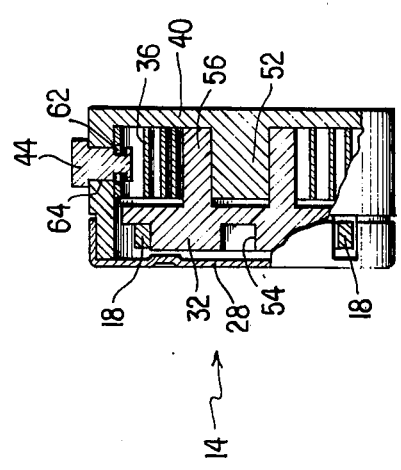

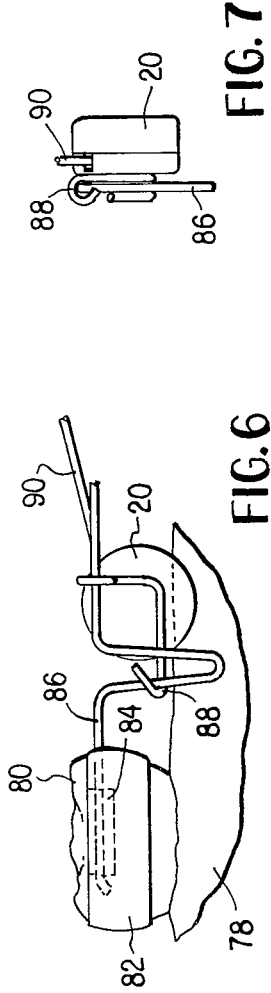
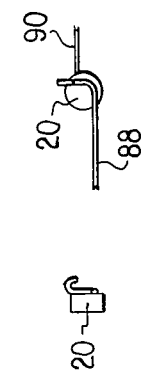
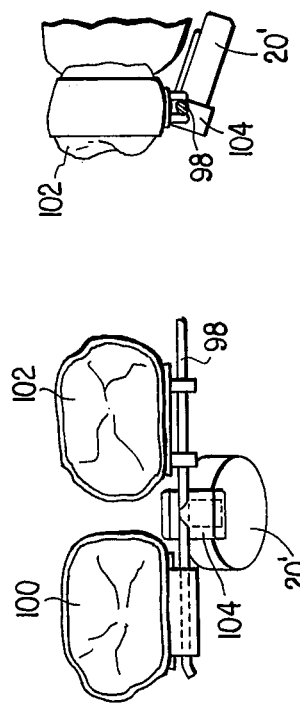
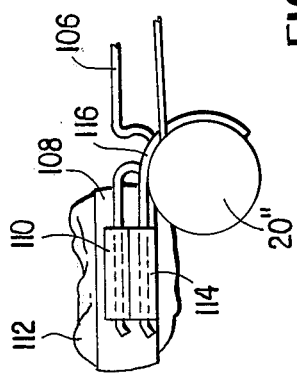
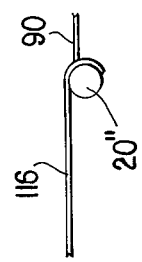
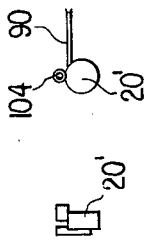

INTERMAXILLARY TOOTH MOVING DEVICE

This invention is directed to an orthodontic appliance and more particularly relates to an intermaxillary spring appliance for automatically moving teeth with a constant force.

During orthodontic treatment, it is desirable to exert a force between an anchor tooth and a tooth undergoing correction to cause movement of one or sometimes both of the teeth. Ideally, a tooth will move most efficiently if a constant force is exerted throughout the entire period of movement. In some prior appliances this force has been provided by rubber bands and in others by extension springs. The limited durability of rubber bands constitutes a disadvantage for this type of appliance and both the rubber bands and conventionally used springs tend to have decaying force as the tooth or teeth undergoing correction move. Since the force applied by conventional springs is directly proportional to their linear extension, frequent manipulation of the appliance by the orthodontist is necessary to produce the desired force.

In order to overcome this problem, it has been proposed in U.S. Pat. No. 3,654,702 to provide a constant or non-cumulative force spring. Another device for overcoming this problem is disclosed in assignee's U.S. Pat. No. 3,921,295 in the form of one or more devices located intermediate the teeth to which it is attached. While producing a near constant tension along the pull cable, devices of the type disclosed in assignee's patent exhibits a very limited range of linear travel and are not suited for intermaxillary application.

In the present invention the increased travel requirements are met by providing a pair of spring loaded devices, that is, one at both ends of the pole, so that the travel is increased without at the same time having a large appliance in the mouth. Each end of the pole is provided with a housing having a rotatable pulley over which the respective end of the pole cable is wrapped. A coil spring biases the pulley and is connected at one end of a slot in the exterior surface of the pulley and is restrained at its other end by a pin passing through a suitable aperture in the housing. Enlargements at each end of the pole cable establish the initial bias for the respective springs and aids in the assembly of the two devices with their counter acting spring forces. The devices may be connected to teeth on the upper and lower jaws in a variety of ways at the option of the orthodontist.

It is therefore one object of the present invention to provide an improved orthodontic appliance.

Another object of the present invention is to provide an improved intermaxillary tooth moving device.

Another object of the present invention is to provide an orthdontic device in the form of a pull cable with counter acting springs at each end.

Another object of the present invention is to provide an intermaxillary tooth positioning or moving device which automatically applies a constant force to the teeth.

Another object of the present invention is to provide an intermaxillary orthodontic appliance which meets the intermaxillary travel requirements without introducing an exceptionally large device into the mouth.

These and further objects and advantages of the invention will be more apparent upon reference to the following specification, claims and appended drawings wherein:

FIG. 4 is an elevational view with partial sections through each of the spring elements illustrating their construction;

FIG. 5 is a partial cross-section through one of the spring elements taken at right angles to the view of FIG. 4;

FIG. 6 is an elevational view of a portion of a human mouth showing the manner of connecting one of the housings of the device of this invention to a tooth;

FIG. 7 is a view of the connecting structure taken at right angles to FIG. 6;

FIG. 8 is a view showing the connection of FIG. 7 at actual size;

FIG. 9 is a right angle view of the connection at actual size;

FIG. 10 is a view of a modified arrangement for connecting the device to teeth in a human mouth;

FIG. 11 is a view taken at right angles to that of FIG. 10;

FIG. 12 is an actual size view of the connection;

FIG. 13 is an actual size view taken at right angles to FIG. 12;

FIG. 14 is a view showing a still further modified arrangement for connecting one of the spring members to a human tooth;

FIG. 15 is an actual size view of the connection; and

FIG. 16 is an actual size view taken at right angles to FIG. 15.

Figure 1:
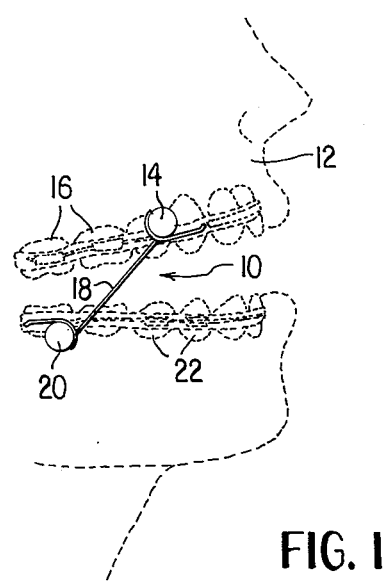
FIG. 1 is a diagrammatic view of a human mouth showing the intermaxillary orthodontic appliance of the present invention applied to the upper and lower jaws.
Figure 2:
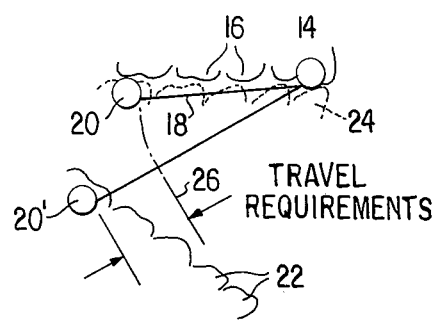
FIG. 2 illustrates the rather substantial travel requirements met by the intermaxillary device of this invention.

Referring to the drawings, the intermaxillary appliance of the present invention is generally indicated at 10 in FIG. 1 as applied to the jaws of a human face diagrammatically indicated by the dashed lines 12. One spring element 14 of cylindrical configuration is illustrated as connected to one or more of the upper set of teeth 16 and this unit is connected by a pull cable 18 to a lower unit 20 again connected to one or more of a lower set of teeth 22. FIG. 2 illustrates the travel requirement or extremes of extension which must be met by the device between the closed jaw illustrated by the dashed lower teeth at 24 and the solid line position of the lower teeth 22. The distance the pull cable 18 must stretch is the distance from the curve line 26 to the lower device when in the jaw open position as illustrated at 20' in FIG. 2. This extension is substantially greater than any normal movement and corresponding cable extension requirement for appliances applied to teeth on the same jaw. The intermaxillary travel requirements as illustrated in FIG. 2 are much greater.

Figure 3:
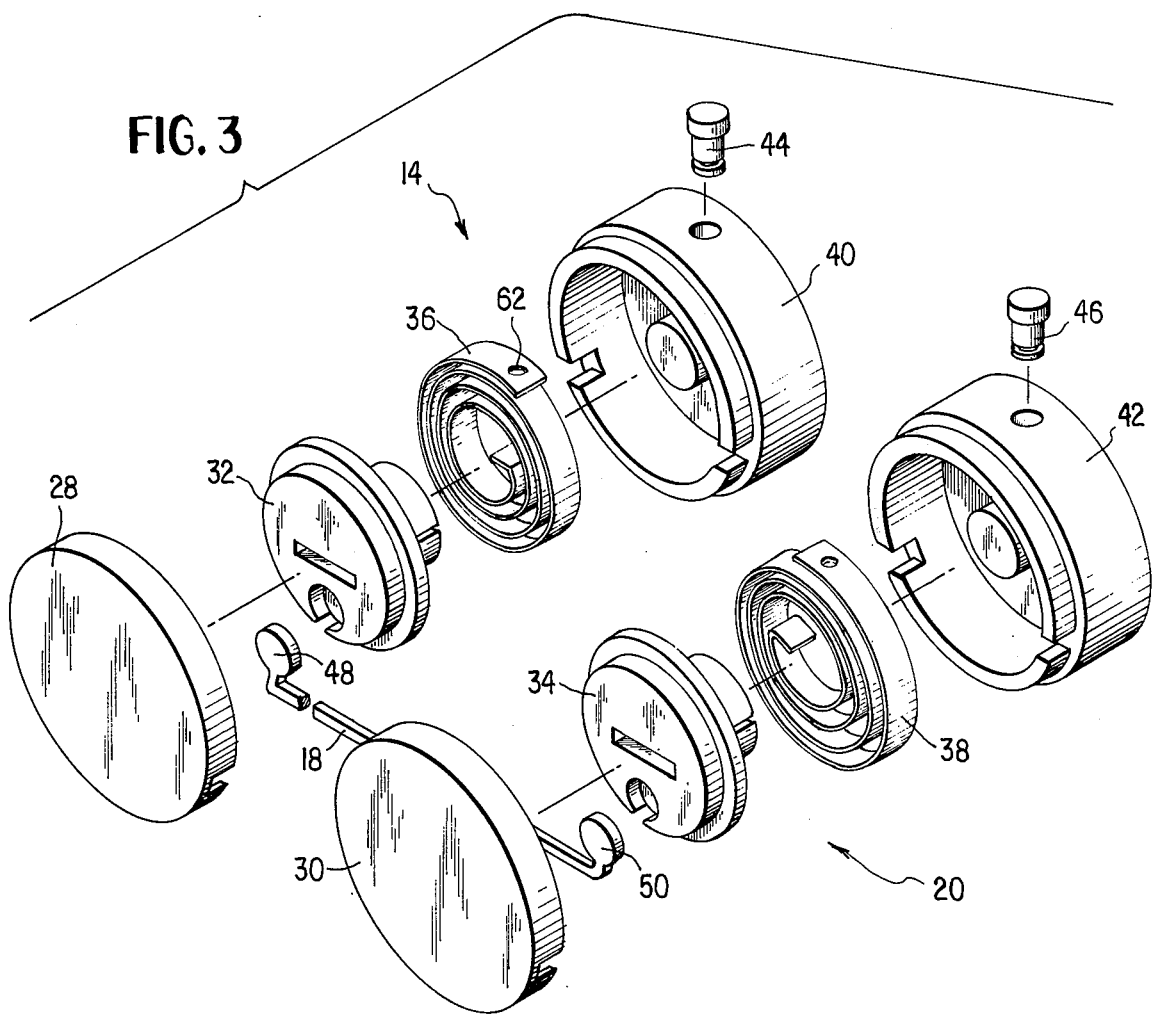
FIG. 3 is an exploded view showing the elements of each of the spring units of the device.

FIG. 3 is an exploded view showing the elements of the upper device 14 and the lower jaw device 20 which are in fact of identical construction. They include the corresponding covers 28 and 30, pulleys 32 and 34, spiral springs 36 and 38, and housings 40 and 42. The outer end of each spring is secured to its respective housing by the corresponding pins 44 and 46. Pull cable 18 is of course common to both of the devices and has corresponding enlarged ends 48 and 50.

As is apparent from the exploded view of FIG. 3, the two elements 14 and 20 are of identical construction. However, when assembled the springs are wound in opposite directions and the pull cable ends are wound in corresponding opposite directions about their respective pulleys. FIG. 4 shows the assembled construction with parts in cross section and FIG. 5 is a partial section through the upper element 14.

As illustrated in FIGS. 4 and 5, unit 14 comprises a housing 40 to which is attached the cover 28. The housing includes a central circular extension or boss 52 on which is rotatably mounted the pulley 32. The pulley is provided with a slot 54 adapted to receive a tool such as the end of the screw driver so that the pulley may be manually rotated on boss 52. A narrow diameter portion 56 of the pulley surrounds the boss and this is provided with a groove 58 as best seen in FIG. 4 receiving a turned over end 60 of the spiral spring 36. This secures the inner end of the spring to the pulley 32. The outer end of the spring is provided with a slot 62 through which passes the inner end of pin 44 so that the pin secures the outer end of the sprial spring to the housing 40. The housing is suitably apertured as at 64 to pass the pin 44. Pull cable 18 is wound around a shoulder formed on the enlarged diameter section 66 of pulley 32.

The only difference between the elements 14 and 20 of FIG. 4 is that the spring 36 of element 14 is inserted over the pulley with its winding in one direction, such as, for example, counter clockwise, from inner to outer end whereas the spring 38 of element 20 is inserted so that its windings travel in the opposite direction, i.e., clockwise, from inner end to outer end of the spring. The opposite ends of the pull cable including the enlargements 48 and 50 are similarly wound around the pulley in opposite directions. Bulges 70 and 72 on the pull cable control the initial tension on the spring since they will not pass through the respective housings 40 and 42. However, the housings are provided with a pair of slots which pass the ends of the cables, one of these slots being shown at 74 in FIG. 4, it being understood that a corresponding aperture is provided on the diametrically opposite side of the housing so that the housings are completely interchangeable and one slot used when the housing forms a left hand member such as illustrated at 20 in FIG. 4 and the other slot or aperture used to pass the cable when the housing is used for a right hand element such as the element 14 in FIG. 4.

FIG. 6 shows one manner of connecting one of the devices of the present invention in a human mouth. FIG. 6 shows a portion of a lower jaw at 78 from which extends an anchor tooth 80 to which is applied a band 82 and bracket shown in dashed lines at 84 in a conventional manner. An arch wire 86 is shown as extending from the bracket and this is secured by a tie wire 88. Attached to the tie wire is the device 20. FIGS. 8 and 9 are end and side views respectively of the device 20 of the FIGS. 6 and 7 drawn to actual size with the tie wire 88 secured to it but before attachment to the arch wire.

FIGS. 10 and 11 show a modified form of attachment in which an arch wire 98 is shown as connected by suitable bracket and bands to a pair of anchor teeth 100 and 102. The device 20' is provided with a screw clamp 104 through which the arch wire 98 passes and by means of which the device is connected to the arch wire. The screw clamp is secured to the housing 42 and is attached to the arch wire intermediate the teeth. The construction to actual size is illustrated in FIGS. 12 and 13.

FIG. 14 shows a modified attachment arrangement in which an arch wire 106 is connected by a band 108 and bracket 110 to an anchor tooth 112. In this embodiment the band 108 is provided with an additional bracket 114 which receives one end of a wire 116. The other end of this separate wire which is approximately of the consistency of the arch wire 106 is connected to the housing of the device 20'. Again FIGS. 15 and 16 are front and side views respectively of the embodiment of FIG. 14 drawn to actual size.

Referring to FIGS. 4 and 5, the device is assembled by first welding the appropriate mounting brackets pursuant to one of the mounting arrangements shown in FIGS. 6–16 to the respective housings 40 and 42. Then for the device 14 the mainspring 36 is inserted into the housing. The pulley 32 is then positioned on the shaft or boss in the housing and the hook at the hub end of the mainspring is inserted into the slot in the pulley. Pin 44 is then pushed through the hole in the housing 40. The pulley is manually rotated causing the spring to drag around inside the housing until the pin catches in the hole such as the hole 62 in the outer end of the spring thereby locking the spring to the pin and housing. The pulley is manually rotated with a suitable torque device until the spring is wound to the desired tension. The pull cable is then inserted with the enlargement into a suitable slot in the pulley and wound around the pulley and exited through the slot 74 in the housing. The bulge 70 in the pull cable keeps the torqued spring from turning the pulley which would result in the cable being drawn into the housing. The cover is then positioned on the housing and secured in place in any suitable manner such as by welding or by adhesive. These steps are then repeated for the other device 20 and the double unit is completed.

It is apparent from the above that the present invention provides an improved intermaxillary orthodontic device and more particularly a device for automatically moving teeth with a constant force. This is made possible by providing two units joined by an intermediate pull cable so that the travel requirements of an intermaxillary device can be met without placing an unduly large appliance in the mouth. By suitable rotation of the pulleys during assembly in conjunction with the location of the bulges or rings on the pull cable, it is possible to pre-adjust or pre-tension the springs the desired amount so that irrespective of the position of the jaws an at least substantially constant force is exerted by one or the other or both springs tending to improve overall tooth movement.

The invention may be embodied in other specific forms without departing from the spirit or essential characteristics thereof. The present invention is, therefore, to be considered in all respects as illustrative and not restrictive, the scope of the invention being indicated by the appended claims rather than by the foregoing description and all changes which come within the meaning and range of equivalency of the claims are, therefore, intended to be embraced therein.

What is claimed and desired to be secured by United States Letters Patent is:

1. An orthodontic appliance for intermaxillary tooth correction comprising a pair of housings, a pulley rotatable inside each said housing, means for coupling said pulleys together including a cable end wrapped around each pulley and extending outwardly from each housing, and a spring in each housing coupled to said pulley for applying a bias force to said pulley tending to draw said cable ends into said respective housings, said cable ends having enlargements for preventing them from being wholly drawn into said housings.

2. An orthodontic appliance according to claim 1 wherein said means for coupling said pulleys together comprises a common pull cable.

3. An orthodontic appliance according to claim 1 wherein each said spring is a spiral spring.

4. An orthodontic appliance according to claim 3 wherein each said spiral spring is connected at its outer end to said housing and at its inner end to said pulley.

5. An orthodontic appliance according to claim 4 wherein the inner end of said spring is turned over, said pulley having a slot receiving the turned over end of said spring.

6. An orthodontic appliance according to claim 5 wherein the outer end of said spring includes a slot, said housing including a pin extending into said slot.

7. An orthodontic appliance for intermaxillary tooth correction comprising a pair of housings, a pulley rotatable inside each said housing, means for coupling said pulleys together including a cable end wrapped around each pulley and extending outwardly from each housing, one of said cable ends being wrapped around its pulley in a clockwise direction and the other in a counterclockwise direction, a spring in each housing coupled to its respective pulley for applying a bias force to said pulley tending to draw said cable ends into said respective housings, said cable ends having enlargements for preventing them from being wholly drawn into said housings.

8. An orthodontic appliance according to claim 7 wherein each said housing is of cylindrical configuration closed at one end, and a cover closing off the other end of said housing.

9. An orthodontic appliance according to claim 8 wherein each said pulley has an enlarged diameter portion around which said cable end is wrapped.

10. An orthodontic appliance according to claim 8 wherein said enlarged diameter portion of said pulley is adjacent said cover.

11. An orthodontic appliance according to claim 10 wherein said pulley includes a smaller diameter portion, said spring coupling said housing to said smaller diameter portion of said pulley.

12. An orthodontic appliance according to claim 11 wherein said spring comprises a spiral spring having its outer end connected to said housing and its inner end connected to said smaller diameter portion of said pulley.

13. An orthodontic appliance according to claim 12 wherein each of said spiral springs is wound in a different direction in accordance with the clockwise and counterclockwise directions of said cable ends.

14. An orthodontic appliance according to claim 13 wherein said smaller diameter portion of said pulley has a slot, each said spring including a turned over inner end received in said slot.

15. An orthodontic appliance according to claim 14 wherein the outer end of each said spring includes an aperture, said housing including a plug having its inner end received through said aperture.

16. An orthodontic appliance according to claim 7 including a wire connected to at least one of said housings for mounting the housing in a human mouth.

17. An orthodontic appliance according to claim 16 wherein said wire is a tie wire for an arch wire.

18. An orthodontic appliance according to claim 7 including a mounting ring connected to at least one of said housings for supporting it in a human mouth.

* * * * *